US00PP24255P2

(12) United States Plant Patent
van der Knaap

(10) Patent No.: US PP24,255 P2
(45) Date of Patent: Feb. 18, 2014

(54) *KALANCHOE* PLANT NAMED 'KATARORE'

(50) Latin Name: *Kalanchoe hybrida*
Varietal Denomination: Katarore

(75) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 139 days.

(21) Appl. No.: 13/385,436

(22) Filed: Feb. 17, 2012

(51) Int. Cl.
*A01H 5/00* (2006.01)

(52) U.S. Cl.
USPC ..... Plt./341

(58) Field of Classification Search
USPC ..... Plt./341, 335
See application file for complete search history.

*Primary Examiner* — June Hwu
(74) *Attorney, Agent, or Firm* — C. A. Whealy

(57) ABSTRACT

A new and distinct cultivar of *Kalanchoe* plant named 'Katarore', characterized by its upright, uniform and moderately vigorous growth habit; freely branching habit; deeply serrated leaves; uniform and freely flowering habit; double dark red-colored flowers; and excellent postproduction longevity.

2 Drawing Sheets

Botanical designation: *Kalanchoe hybrida.*
Cultivar denomination: 'KATARORE'.

BACKGROUND OF THE INVENTION

The present invention relates to a new and distinct cultivar of *Kalanchoe* plant, botanically known as *Kalanchoe hybrida* and hereinafter referred to by the name 'Katarore'.

The new *Kalanchoe* plant is a product of a planned breeding program conducted by the Inventor in Naaldwijk, The Netherlands. The objective of the breeding program is to create new double-flowered *Kalanchoe* plants with attractive foliage shapes and flower coloration.

The new *Kalanchoe* plant originated from a cross-pollination made by the Inventor in Naaldwijk, The Netherlands in November, 2005 of a proprietary selection of *Kalanchoe hybrida* identified as code number 20051047-001, not patented, as the female, or seed parent with a proprietary selection of *Kalanchoe hybrida* identified as code number 20021234-001, not patented, as the male, or pollen, parent. The new *Kalanchoe* plant was discovered and selected by the Inventor as a flowering plant from within the progeny of the stated cross-pollination in a controlled greenhouse environment in Naaldwijk, The Netherlands in September, 2006.

Asexual reproduction of the new *Kalanchoe* plant by vegetative terminal cuttings in a controlled greenhouse environment in Naaldwijk, The Netherlands since May, 2007 has shown that the unique features of this new *Kalanchoe* plant are stable and reproduced true to type in successive generations.

SUMMARY OF THE INVENTION

Plants of the new *Kalanchoe* have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Katarore'.

These characteristics in combination distinguish 'Katarore' as a new and distinct *Kalanchoe* plant:

1. Upright, uniform and moderately vigorous growth habit.
2. Freely branching habit.
3. Deeply serrated leaves.
4. Uniform and freely flowering habit.
5. Double dark red-colored flowers.
6. Excellent postproduction longevity.

Plants of the new *Kalanchoe* can be compared to plants of the female parent selection. Plants of the new *Kalanchoe* differ primarily from plants of the female parent selection in the following characteristics:

1. Plants of the new *Kalanchoe* are smaller than plants of the female parent selection.
2. Plants of the new *Kalanchoe* are more freely branching than plants of the female parent selection.
3. Plants of the new *Kalanchoe* have smaller leaves than plants of the female parent selection.
4. Plants of the new *Kalanchoe* and the female parent selection differ in flower color as plants of the female parent selection have purple-colored flowers.

Plants of the new *Kalanchoe* can also be compared to plants of the male parent selection. Plants of the new *Kalanchoe* differ from plants of the male parent selection in the following characteristics:

1. Plants of the new *Kalanchoe* are larger than plants of the male parent selection.
2. Flowers of plants of the new *Kalanchoe* are double whereas flowers of plants of the male parent selection are single.
3. Plants of the new *Kalanchoe* and the male parent selection differ in flower color as plants of the male parent selection have red purple-colored flowers.

Plants of the new *Kalanchoe* can be compared to plants of the *Kalanchoe blossfeldiana* 'Don Juan', disclosed in U.S. Plant Pat. No. 17,576. In side-by-side comparisons conducted in Naaldwijk, The Netherlands, plants of the new *Kalanchoe* differed from plants of 'Don Juan' in the following characteristics:

1. Plants of the new *Kalanchoe* were more compact than plants of 'Don Juan'.
2. Plants of the new *Kalanchoe* had smaller leaves than plants of 'Don Juan'.
3. Plants of the new *Kalanchoe* and 'Don Juan' differed in flower color as flowers of plants of 'Don Juan' were lighter red in color.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet comprises a side perspective view of a typical flowering plant of 'Katarore' grown in a container.

The photograph on the second sheet are close-up views of upper and lower surfaces of typical flowers (top), a typical inflorescence (center) and the upper and lower surfaces of typical leaves (bottom).

DETAILED BOTANICAL DESCRIPTION

The aforementioned photographs and following observations, measurements and values describe plants grown during the winter in 12-cm containers in a glass-covered greenhouse in Naaldwijk, The Netherlands and under conditions which closely approximate commercial *Kalanchoe* production. During the production of the plants, day temperatures ranged from 20° C. to 30° C., night temperatures ranged from 18° C. to 25° C. and light levels ranged from 5 to 60 kilolux. Plants received long day/short night conditions (more than 14 hours of light) for about four weeks; plants then received photoinductive short day/long night conditions (minimum 14 hours darkness) until flowering. Plants were 13 weeks old when the photographs and the description were taken. In the detailed description, color references are made to The Royal Horticultural Society Colour Chart, 2007 Edition, except where general terms of ordinary dictionary significance are used.

Botanical classification: *Kalanchoe hybrida* 'Katarore'.

Parentage:

*Female, or seed, parent.*—Proprietary selection of *Kalanchoe hybrida* identified as code number 20051047-001, not patented.

*Male or pollen parent.*—Proprietary selection of *Kalanchoe hybrida* identified as code number 20021234-001, not patented.

Propagation:

*Type.*—By vegetative terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About three weeks at temperatures of 21° C.

*Time to produce a rooted young plant, winter.*—About four weeks at temperatures of 21° C.

*Root description.*—Fine, fibrous; white in color.

*Rooting habit.*—Freely branching; dense.

Plant description:

*Plant habit.*—Upright, uniform and moderately vigorous growth habit with rounded crown; freely flowering with numerous compound cymes; appropriate for 12-cm and larger containers.

*Plant height at flowering.*—About 16.5 cm.

*Plant diameter at flowering.*—About 23.7 cm.

Lateral branch description:

*Branching habit.*—Freely branching habit; usually about ten lateral branches develop per plant.

*Length.*—About 5.5 cm.

*Diameter.*—About 4 mm.

*Internode length.*—About 1.3 cm.

*Aspect.*—Erect.

*Strength.*—Strong.

*Texture.*—Smooth, glabrous.

*Color.*—Close to 143B.

Foliage description:

*Arrangement.*—Opposite, simple; generally symmetrical.

*Length, generative plants.*—About 8.6 cm.

*Width, generative plants.*—About 3.7 cm.

*Shape.*—Irregularly ovate, lanceolate to oblanceolate.

*Apex.*—Obtuse to bluntly acute.

*Base.*—Cuneate.

*Margin.*—Deeply serrate.

*Texture, upper and lower surfaces.*—Smooth, glabrous, leathery; succulent.

*Venation pattern.*—Pinnate.

*Color.*—Developing leaves, upper surface: Close to N137A. Developing leaves, lower surface: Close to 138A. Fully expanded leaves, upper surface: Close to N137A to N137B; venation, close to N137B. Fully expanded leaves, lower surface: Close to 147B; venation, close to 138A.

*Petiole.*—Length: About 1.5 cm. Diameter: About 4 mm to 4.5 mm. Texture, upper and lower surfaces: Smooth, glabrous. Color, upper surface: Close to 143A. Color, lower surface: Close to 143B.

Flower description:

*Flower arrangement and habit.*—Double flowers arranged singly in compound dichasial cymes arising from leaf axils; uniform and freely flowering habit with usually about 50 flowers developing per inflorescence.

*Fragrance.*—None detected.

*Natural flowering season.*—Plants of the new *Kalanchoe* flower from spring through autumn in the garden; flower initiation and development can be induced under artificial short day/long night conditions (at least 14 hours of darkness).

*Time to flower.*—Under short day/long night photoinductive conditions, about 60 days are required.

*Post-production longevity.*—Excellent post-production longevity; flowers maintain good substance for about seven weeks under interior environmental conditions; individual flowers last about ten days on the plant; flowers persistent.

*Inflorescence height.*—About 5 cm.

*Inflorescence diameter.*—About 5.6 cm.

*Flower diameter.*—About 2.1 cm.

*Flower length (height).*—About 1.8 cm.

*Flower bud.*—Length: About 9 mm. Diameter: About 4 mm. Shape: Oblong to narrowly obovate. Color: Close to 143B; towards the apex, close to 39B.

*Petals.*—Quantity and arrangement: About 24 arranged in several whorls. Length: About 1.4 cm to 1.9 cm. Width: About 4 mm to 9 mm. Shape: Obovate; occasionally upper half of petal is cleft. Apex: Abruptly acute to cleft. Margin: Entire. Texture, upper and lower surfaces: Smooth, glabrous; velvety. Color: When opening and fully opened, upper surface: Close to 53A; towards the base, close to 143B; color does not fade with development. When opening and fully opened, lower surface: Close to 54B; center, close to 145D; towards the base, close to 143B.

*Sepals.*—Quantity and appearance: Four, fused at the base. Length: About 8 mm. Width: About 3 mm. Shape: Broadly lanceolate. Apex: Acute. Margin: Entire. Texture, upper and lower surfaces: Smooth; glabrous. Color: Immature and mature, upper surface: Close to 143B. Immature and mature, lower surface: Close to 143C.

*Peduncles.*—Length: About 3.8 cm. Diameter: About 4 mm. Aspect: Mostly erect. Strength: Moderately strong. Texture: Smooth, glabrous. Color: Close to 143B to 143C.

*Pedicels.*—Length: About 4 mm. Diameter: About 1.5 mm. Aspect: Erect to about 35° from vertical. Strength: Moderately strong. Texture: Smooth, glabrous. Color: Close to 143C.

*Reproductive organs.*—Androecium: Stamen number: About four per flower. Filament length: About 5 mm. Filament color: Close to 145A. Anther length: About 0.4 mm. Anther shape: Oblong. Anther color: Close to 152B. Amount of pollen: Scarce. Pollen color: Close to 11A. Gynoecium: Pistil number: About four per flower. Pistil length: About 6.5 mm. Style length: About 6 mm. Style color: Close to 145A. Stigma shape: Club-shaped. Stigma color: Close to 150B to 150C. Ovary color: Close to 145B to 145C.

*Seeds and fruits.*—Seed and fruit development has not been observed on plants of the new *Kalanchoe.*

Temperature tolerance: Plants of the new *Kalanchoe* have been observed to tolerate temperatures from about 5° C. to about 35° C.

Pathogen & pest resistance: Plants of the new *Kalanchoe* have not been observed to be resistant to pests and pathogens common to *Kalanchoes.*

It is claimed:

1. A new and distinct *Kalanchoe* plant named 'Katarore' as illustrated and described.

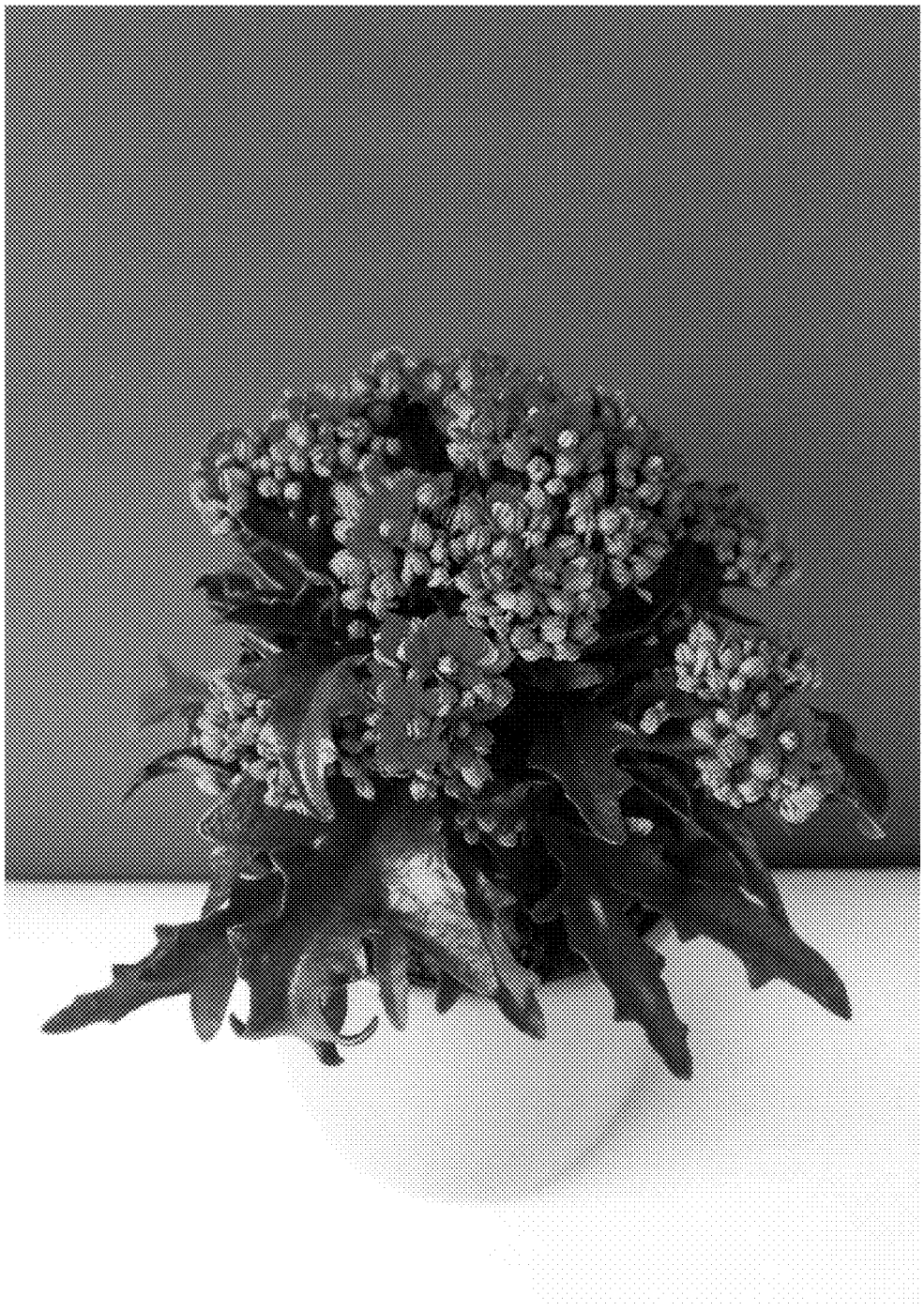

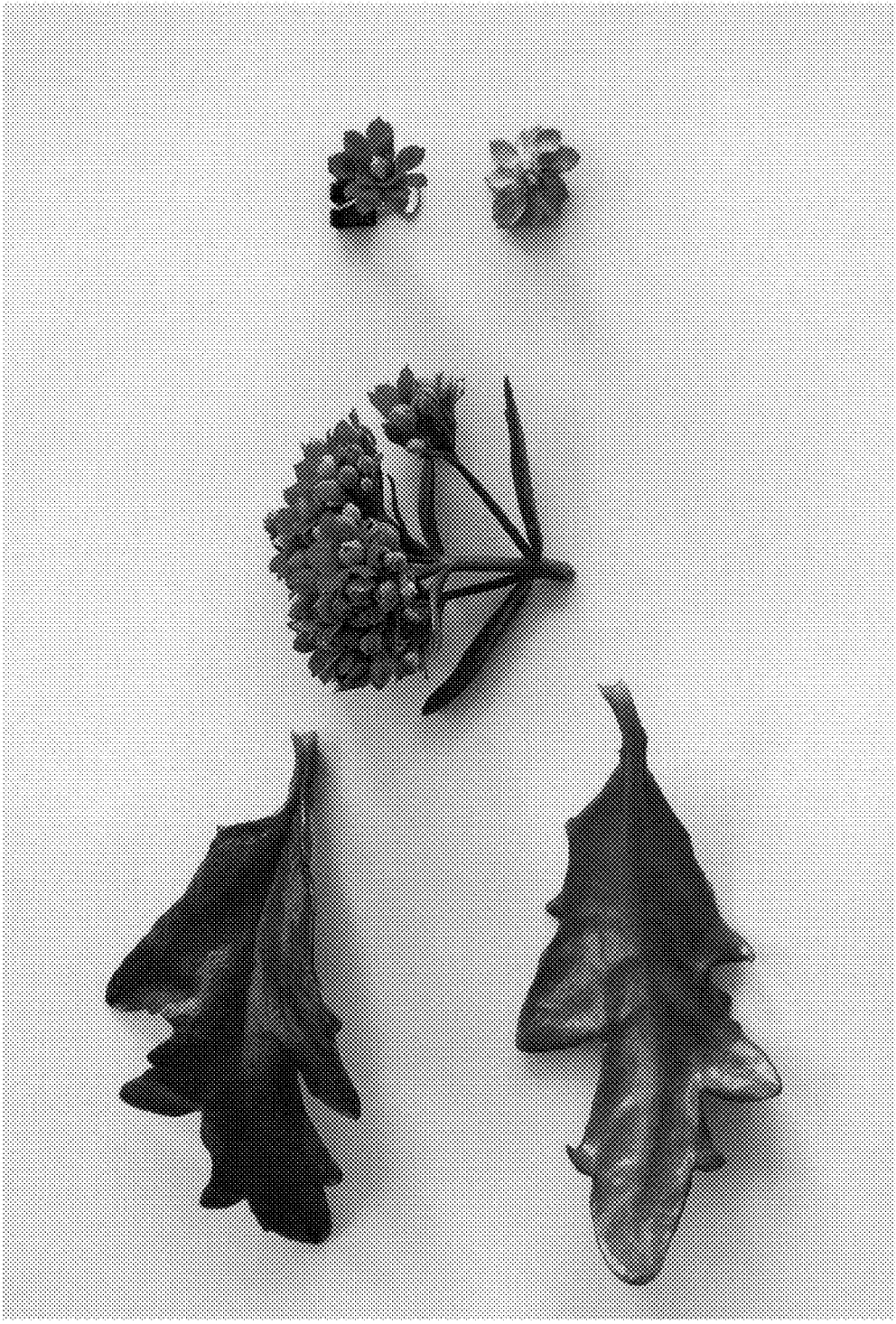

* * * * *